United States Patent
Koerber et al.

(10) Patent No.: US 10,137,401 B2
(45) Date of Patent: *Nov. 27, 2018

(54) OXYGEN SEPARATOR WITH RAPID DIAGNOSTIC

(71) Applicant: KONINKLIJKE PHILIPS N.V., Eindhoven (NL)

(72) Inventors: Achim Gerhard Rolf Koerber, Eindhoven (NL); Rainer Hilbig, Aachen (DE); Paul Van Der Sluis, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 87 days.

This patent is subject to a terminal disclaimer.

(21) Appl. No.: 15/105,605

(22) PCT Filed: Dec. 20, 2014

(86) PCT No.: PCT/EP2014/078936
§ 371 (c)(1),
(2) Date: Jun. 17, 2016

(87) PCT Pub. No.: WO2015/092063
PCT Pub. Date: Jun. 25, 2015

(65) Prior Publication Data
US 2016/0310886 A1    Oct. 27, 2016

(30) Foreign Application Priority Data
Dec. 20, 2013 (EP) .................................... 13198706

(51) Int. Cl.
*B01D 53/04* (2006.01)
*B01D 53/047* (2006.01)
(Continued)

(52) U.S. Cl.
CPC ......... *B01D 53/047* (2013.01); *A61M 16/101* (2014.02); *A62B 7/08* (2013.01);
(Continued)

(58) Field of Classification Search
CPC .. B01D 53/047; B01D 53/30; B01D 2256/12; B01D 2257/102; B01D 2259/40009;
(Continued)

(56) References Cited

U.S. PATENT DOCUMENTS 3,142,547 A    7/1964 Marsh
4,077,780 A *  3/1978 Doshi .................. B01D 53/047
                                                95/100
(Continued)

FOREIGN PATENT DOCUMENTS

EP    1114666 A2     7/2001
JP    2008195556 A   8/2008
WO    WO9856488 A1   12/1998

OTHER PUBLICATIONS

Yaping Lu et al., "Tuning of Pressure Swing Adsorption Systems Based on Differential Pressure Profile", 2005 Springer Science + Business Media, Inc. Manufactured in The Netherlands, Adsorption 11: 315-324, 2005, pp. 315-324.

*Primary Examiner* — Frank M Lawrence, Jr.
(74) *Attorney, Agent, or Firm* — Michael W. Haas (57) ABSTRACT

The invention relates to an oxygen separator for generating a flow of oxygen-enriched gas, said oxygen separator comprising at least two oxygen separation devices arranged to separate oxygen from an oxygen comprising gas, said at least two oxygen separation devices each comprising a first end for receiving the oxygen comprising gas and a second end for delivering an oxygen-enriched gas. The oxygen separator further comprising an equalization duct fluidically coupled to the respective second end of said at least two oxygen separation devices, a first gas sensor is provided in (Continued)

the equalization duct such that the first gas sensor is arranged to monitor at least one component of the oxygen-enriched gas in the equalization duct; and control device arranged to control the oxygen separator based on the monitoring by the first gas sensor.

14 Claims, 3 Drawing Sheets

(51) Int. Cl.
| | | |
|---|---|---|
| *B01D 53/30* | (2006.01) | |
| *C01B 13/02* | (2006.01) | |
| *A61M 16/10* | (2006.01) | |
| *A62B 7/08* | (2006.01) | |
| *A62B 7/14* | (2006.01) | |

(52) U.S. Cl.
CPC .......... *B01D 53/30* (2013.01); *C01B 13/0259* (2013.01); *A62B 7/14* (2013.01); *B01D 2256/12* (2013.01); *B01D 2257/102* (2013.01); *B01D 2259/40009* (2013.01); *B01D 2259/40035* (2013.01); *B01D 2259/4533* (2013.01)

(58) Field of Classification Search
CPC . B01D 2259/40035; B01D 2259/4533; A61M 16/101; A62B 7/08; A62B 7/14; C01B 13/0259
USPC ............. 95/8, 12, 96, 130; 96/109, 111, 121
See application file for complete search history.

(56) References Cited

U.S. PATENT DOCUMENTS

| | | | |
|---|---|---|---|
| 4,449,990 A | | 5/1984 | Tedford, Jr. |
| 4,693,730 A | | 9/1987 | Miller |
| 4,732,578 A | * | 3/1988 | Benkmann ........... B01D 53/047 |
| | | | 95/130 |
| 5,013,334 A | * | 5/1991 | Maurer ................... B01D 53/02 |
| | | | 95/100 |
| 5,529,607 A | | 6/1996 | Tan |
| 5,906,672 A | * | 5/1999 | Michaels ............. B01D 53/047 |
| | | | 95/12 |
| 7,329,304 B2 | | 2/2008 | Bliss |
| 7,445,663 B1 | | 11/2008 | Hunter |
| 2006/0230929 A1 | | 10/2006 | Bliss |
| 2006/0288867 A1 | * | 12/2006 | Herb .................... B01D 53/047 |
| | | | 95/96 |
| 2007/0204748 A1 | * | 9/2007 | Lomax, Jr. .......... B01D 53/047 |
| | | | 95/96 |
| 2008/0066616 A1 | | 3/2008 | Sprinkle |
| 2011/0247622 A1 | | 10/2011 | Schneider |
| 2012/0234165 A1 | | 9/2012 | Elseviers |
| 2012/0234173 A1 | | 9/2012 | Phuc |
| 2013/0042754 A1 | * | 2/2013 | Lomax ................. B01D 53/047 |
| | | | 95/19 |
| 2016/0310887 A1 | * | 10/2016 | Van Der Sluis ... G01N 25/4873 |

* cited by examiner

OXYGEN SEPARATOR WITH RAPID DIAGNOSTIC

CROSS-REFERENCE TO RELATED APPLICATIONS

This patent application claims the priority benefit under 35 U.S.C. § 371 of international patent application no. PCT/EP2014/078936, filed Dec. 20, 2014, which claims the benefit of European Patent Application No. EP13198706.7, filed on Dec. 20, 2013, which is hereby incorporated by reference herein.

FIELD OF THE INVENTION

The invention relates to the field of oxygen separation. More specifically, the invention relates to an apparatus using at least two oxygen separation devices arranged to separate oxygen from an oxygen comprising gas. Said at least two oxygen separation devices comprise respectively a first end for receiving the oxygen comprising gas and a second end for delivering an oxygen-enriched gas, wherein an equalization duct is fluidically coupled to the respective second end of said at least two oxygen separation devices.

The invention further relates to a method for separating oxygen from an oxygen comprising gas the method comprising the steps of operating an oxygen separator for generating an oxygen-enriched gas, said oxygen separator comprising at least two oxygen separation devices to separate oxygen from an oxygen comprising gas and equalizing the oxygen separator by generating an equalization flow of oxygen-enriched gas in an equalization duct, said equalization duct fluidically coupling the respective second ends of the at least two separation devices;

BACKGROUND OF THE INVENTION

Oxygen therapy is the administration of oxygen as a therapeutic intervention. Oxygen therapy may be used for a variety of interventions in both chronic and acute user care where an increased supply of oxygen to the lungs is needed, hence increasing the availability of oxygen to different body tissues. Oxygen therapy may be used in different environment settings including hospital and/or home depending on a user's needs.

In order to provide a user with an oxygen-enriched gas, numerous ways of administration have been suggested. A known way to provide a user with an oxygen-enriched gas is by an oxygen concentrator. Oxygen concentrators are commercially available and offered in different sizes and efficiencies as to fulfill distinctive user's needs. Those oxygen concentrators are capable of separating oxygen from ambient air, therefore providing a user with an oxygen-enriched gas and venting a nitrogen-enriched gas in the surrounding of said oxygen concentrator. Those known oxygen concentrators may provide for an "on-demand" or a continuous flow of oxygen-enriched gas.

A method for separating oxygen from an oxygen comprising gas by an oxygen concentrator is known from WO1998/56488. This document discloses that a gaseous mixture is supplied under pressure to a bed of a physical separation medium which adsorbs at least one adsorbable component and passes at least one substantially nonadsorbable component of the mixture while a second bed is being evacuated. Before reaching the capacity of the gaseous mixture supplied bed to adsorb the adsorbable component, the beds are brought toward pressure equilibrium by allowing the gas to flow (i.e., to be in fluid communication) between the beds. While a gas flow is guided between the beds, the supply of the gaseous mixture and the evacuation of the beds are reversed. That is, the gaseous mixture is supplied to the heretofore evacuated bed and the heretofore gaseous mixture-supplied bed is evacuated. Subsequent to reversing the supply of the gaseous mixture and the evacuation of the beds, the pressure equalization flow is terminated. These steps are cyclically repeated to provide continuing production of the nonadsorbable component.

It is a drawback of known oxygen concentrators that the oxygen concentration (or the purity) of the oxygen-enriched gas to be provided to the user is adversely affected by modification(s) of the operating conditions of said oxygen concentrators. There is therefore a need to improve oxygen concentrators in order to provide for a stable and continuous oxygen concentration (or purity) of the oxygen-enriched gas to be supplied to the user following modification(s) or alteration(s) of the operating conditions of said oxygen concentrators.

SUMMARY OF THE INVENTION

It is an object of the invention to provide an oxygen separator which is reactive to modifications of the operating conditions of the oxygen separator in order to provide for a stable concentration (or purity) of oxygen in the oxygen-enriched gas to be provided to the user. More specifically, it is an object of the present invention to allow one or more separation devices of the oxygen separator to be operated constantly near their maximum gas separation capacity even following an event where the operating condition of the oxygen separator would be modified and/or altered.

According to the invention, this object is realized in that an equalization duct comprises a gas sensor provided in the equalization duct such that the first gas sensor is arranged to monitor at least one component of an oxygen-enriched gas and a control device arranged to control the oxygen separator based on the monitoring by said gas sensor. Such arrangement provides for a better diagnostics process to control the separation of one compound from a fluid mixture by at least two oxygen separation devices.

This object is further achieved by a method for separating oxygen from an oxygen comprising gas, said method comprising the steps of 1) monitoring by a gas sensor provided in the equalization duct at least one component of the oxygen-enriched gas in the equalization duct and 2) controlling the oxygen separator based on the measuring by the gas sensor via a control device.

The invention is based on the realization that at least two oxygen separation devices for separating an oxygen comprising gas into an oxygen-enriched gas are cyclically in into a "feed" phase and a "purge" phase as further describe below, the cycles being interspersed by an "equalization" phase. This "feed" phase may be described as the phase where, at a given moment, a pressurized oxygen-enriched gas is generated by one oxygen separation device, stored and delivered to a user. This generated oxygen-enriched gas may also be used to ventilate, at a low pressure, the other oxygen separation device; such operation is also known as the "purge" phase. The "feed" and "purge" phases are usually controlled by a number of flow controllers which are controlled by a control device. Typically two oxygen separation devices are filled with suitable selectively adsorbing materials to separate oxygen from an oxygen comprising gas. A sorbent material may thereby be understood as a material which sorbs and thus adsorbs or absorbs at least one compound from a fluid mixture, such as a gaseous mixture or a mixture comprising one or more gases and one or more liquids, much better than at least one further compound of that mixture. It will be understood that the two oxygen separation devices comprise respectively a first end coupled to inlet ducts for guiding a pressurized flow of oxygen comprising gas to enters the respective oxygen separation device and to guide a flow nitrogen-enriched gas outside the oxygen concentrator (in the surrounding of the user) and a second end by which the oxygen-enriched gas is capable of exiting said at least two oxygen separating devices via outlet ducts during a "feed" phase and/or to enter such oxygen separating devices during a "purge" phase.

For example, the oxygen separator may comprise two oxygen separation devices and may thus generally form a pressure swing adsorption (PSA) system. However, the oxygen separator may as well form a vacuum swing adsorption system (VSA) or a vacuum pressure swing adsorption system (VPSA). In an exemplary system, in a first phase of the cycle, the oxygen comprising gas is fed as "inflow" into an oxygen separation device at a high pressure feed ("feed" phase), nitrogen is kept such as adsorbed within this device and oxygen-enriched gas is collected as outflowing "product" in a product tank or receptacle (product side). In a second phase of the cycle the separation device is regenerated, i.e. a purge gas such as a part of the produced oxygen enriched gas, for example, is fed back into the device at a low pressure purge and the previously adsorbed nitrogen is released as exhaust into the surrounding atmosphere ("purge" phase). When two separation devices filled with suitable selectively oxygen separation sorbent are used: while one device is in the "feed" phase producing enriched-oxygen gas at higher pressure, the other device, is in the "purge" phase at lower pressure. After a certain time respectively arranged flow controllers are switched and both devices change their role.

In the interval of the change of phase of an oxygen separation device (i.e.: from a "feed" phase to a "purge" phase or from a "purge" phase to a "feed" phase), an "equalization" phase may occur as to equilibrate the internal pressure of the two oxygen separation devices. A way of achieving such equalization phase is by the absence of pressurized flow of oxygen comprising gas guided to any of the first end of the oxygen separation devices. In an alternative way, a flow of oxygen comprising gas is guided at a low pressure to any of the first end of the oxygen separation devices. Pressure equilibrium is made possible by an equalization duct coupled to the respective second end of the two oxygen separation devices. In detail, the efficiency of a PSA cycle, for example, is increasing if part of the compressed-air energy stored in the first device after the feed phase is re-used for pressurizing the second device to an intermediate pressure. To this purpose, a short "equalization" phase during which both devices are connected at their product side (respective second end) by said equalization duct is inserted between the main phases of the operating cycle.

The invention is advantageous in relation to at last two oxygen separation devices (e.g.: sieve beds) as those are never exactly identical in their separation capacities. As a result of this asymmetry, the one with smaller nitrogen capacity will breakthrough first. A breakthrough is a result of a saturation of the sorbent material which may lead in incapacity of this sorbent material to adsorb (or absorb) the required component. This breakthrough may lead to over increasing oscillations of the whole process which results in a decrease of the oxygen concentration of the oxygen-enriched gas. In other words, such breakthrough results in an increase of the component to be adsorb (or absorb), for example nitrogen, in the product side of the oxygen separator, which could, at its extreme, mean that the concentration of components of the pressurized flow of gas fed to the oxygen separator device is identical, or nearly identical, to the concentration of components in the flow of gas outputted by such oxygen concentration device. The presence of a sensor, preferably a gas sensor, in the equalization duct enables the determination of the onset of these oscillations and provides for relevant information to assess which one of the two oxygen separation devices is falling into breakthrough. With this sensor information, modification of the operating conditions of the oxygen separator may be achieved by the control devise such that the oxygen separator is back into the optimum symmetric operation condition. The resulting sensor signal enables a reliable process diagnostics to control the separation process, in other words to avoid a breakthrough of the nitrogen into the oxygen-enriched gas to be provided to the user.

The use of the sensor signal by the control device allows to reduce fluctuations of the oxygen concentration (or purity) of the oxygen-enriched gas, as a result of one or more modification of the operating conditions, for example temperature or humidity. Such advantage emanates that operating conditions have an effect on the adsorbing capabilities of the sorbent material comprised in the oxygen separation devices.

Another advantage of the invention ensures operating conditions of the oxygen separator at highly efficient operating regimes. A highly efficient operating regime is, for example, a regime where the adiabatic compression power input into the separation devices is low. The use of a sensor into an equalization duct, which is capable of monitoring (for instance detecting, for instance measuring), gas component during the "equalization" phase to detect or monitor possible nitrogen breakthrough may be a prerequisite for operating the PSA system of the at least two oxygen separator devices in the desired highly efficient regimes, as controlled by a control device.

Another advantage of the invention is that operating an oxygen concentration device close to the separation capacity of the oxygen separation devices ensures for a better energy efficiency of the device.

In a preferred embodiment the gas sensor is arranged to monitor (for instance detecting, for instance measuring) the concentration of at least one component of the oxygen-enriched gas in the equalization duct during the "equalization" phase. This arrangement has the advantage of providing for a direct determination of the concentration of the oxygen in the oxygen-enriched gas as to provide for an accurate monitoring of the at least one component during the "equalization" phase, and therefore provides for accurate control, by the control device, of the operating conditions of the system.

In another embodiment, the gas sensor is capable of discrimination between oxygen and nitrogen. This embodiment has the advantage that the sensor allows to measure an increase or decrease of oxygen or nitrogen in the equalization duct during the "equalization" phase. Such embodiment has the advantage of providing for a rapid discrimination of the oxygen-enriched gas information to the control device as the sensor provides for direct monitoring, for example as to the saturation status of the oxygen separation device that was previously into a "feed" phase.

In another embodiment, the control device is capable of controlling at least one parameter that has an effect on the concentration and/or composition and/or purity of the oxygen-enriched gas generated during the "feed" phase. Such at least one parameter enables the oxygen separator to separate the oxygen comprising gas near the maximum gas separation capacity of the oxygen separation devices. This arrangement enables a constant concentration and/or composition and/or purity of the oxygen-enriched gas notwithstanding possible modification(s) of the operating conditions of the oxygen separator. To proceed thereof, it is advisable that the at least one parameter is to be chosen from the group of separation duration, flow controller control, pressure control or separation devices in use.

In another embodiment, the respective first end of each of the at least two oxygen separation devices are fluidically coupled to an exhaust duct to guide a flow of exhaust gas (nitrogen-enriched gas) out of the oxygen separator into the surrounding environment. Such exhaust duct preferably comprises a second gas sensor arranged to monitor (for instance detecting, for instance measuring) at least one component of exhaust gas in such flow of exhaust gas. The second gas sensor provides information related to the gas ventilated from the device such that a second set of data as of the efficiency of the oxygen separator is provided to the control device, or any device. This embodiment has the advantage of providing for an even better diagnostic of the oxygen separation devices to more efficiently control at least one parameter of the oxygen separator. The exhaust duct may be one duct coupled to the respective first end of the oxygen separation device, alternatively it may be two ducts, each ducts respectively coupled to a first end of an oxygen separation device.

In another embodiment, the second gas sensor is arranged to detect the concentration of at least one component of the exhaust gas. This arrangement has the advantage of providing for a direct monitoring of the concentration of the oxygen and/or nitrogen ventilated from the system. This arrangement allows an increase of the accuracy level of the monitoring thereby enabling better diagnostic of the oxygen separator devices as to more efficiently control the parameter of the oxygen separator.

In another embodiment, the control device is arranged to control the oxygen separator based on the monitoring data received by the first gas sensor and by the second gas sensor. Such a second gas sensor monitoring data, combined with the monitoring data of the gas sensor in the equalization duct (first gas sensor), provides the control device with an increase number of relevant monitoring data such that increased control of the oxygen concentrator and oxygen separator parameter(s) that has an effect on the concentration (or purity) of the oxygen-enriched gas generated by the two oxygen separation devices may be achieved. To proceed thereof, it is advisable that the at least one parameter is to be chosen from the group of separation duration, flow controller control, pressure control or separation devices in use.

In another embodiment, the oxygen separator further comprises at least one equalization flow controller (valve) arranged to control a flow of oxygen-enriched gas through the equalization duct. Such equalization flow controller provides for the possibility to open or close or partially allow a flow of enriched oxygen gas into the equalization duct. As a result thereof, the equalization duct may be closed, during the "feed" and/or "purge phases to prevent a decrease of efficiency of the oxygen separator.

In another embodiment, the oxygen separator further comprises a purging duct, said purging duct comprising a purging flow controller arranged to control a flow of oxygen-enriched gas from the second end of one of the at least two oxygen separation devices to the second end of another oxygen separation device during the "purge" phase. An advantage of said purging duct fluidically coupled to the second end of each of the oxygen separation devices is to allow for a dedicated duct during the "purge" phase. Such dedicated duct enables, by at least one flow controller, the sensor of the equalization duct to be solicited exclusively during the "equalization" phase and therefore avoid saturation of said sensor. Alternatively, the equalization duct can also act as a purging duct, wherein it will be acknowledged that the sensor to be used, alternatively the disposition of the sensor, will be chosen such that the sensor is not saturated or affected in other phases than the "equalization" one.

In another embodiment, at least one product flow controller is arranged to control a product flow of oxygen-enriched gas into a reservoir tank or an accumulator. Said reservoir stores oxygen-enriched gas before it is delivered to the user, allowing a constant flow of gas to the user, regardless of the phase in which the oxygen separator is into. This arrangement has namely the advantage of allowing a constant flow of enriched-oxygen gas to the user. Additionally, it allows a further monitoring point of control of one or more parameters of the oxygen separator arranged to be modified as a result of a change in the operating condition of such oxygen separating device.

The method according to the invention is characterized in operating an oxygen separator for generating an oxygen-enriched gas, said oxygen separator comprising at least two oxygen separation devices to separate oxygen from an oxygen comprising gas, equalizing the oxygen separator by generating an equalization flow of oxygen-enriched gas in an equalization duct, said equalization duct fluidically coupling the respective second ends of the at least two separation devices, monitoring with a first gas sensor provided in the equalization duct at least one component of the oxygen-enriched gas in the equalization duct, controlling the oxygen separator based on the determination by the first gas sensor via a control device. This method has the advantage that the resulting sensor signal enables a reliable process diagnostics to control the separation process of the oxygen from an oxygen comprising gas; in other words, said method allows the avoidance of a breakthrough of nitrogen into the oxygen-enriched gas to be essentially provided to the user. Such breakthrough of nitrogen may lead to over increasing oscillations of the whole separation process which results in a decrease of the oxygen concentration (or purity) of the oxygen-enriched gas. The proposed method enables determination of the onset of these oscillations and provides relevant information via sensor data to allow the control device, or any other device, to assess which of the two oxygen separation devices is falling into breakthrough. With this information provided from the signal of a gas sensor into the equalization duct, modification of at least one the operating condition of the oxygen separator by the control device may be achieved such that the oxygen separator and the oxygen separation devices are back into the optimum symmetric operation condition. Moreover, the proposed method allows avoidance of fluctuations of the oxygen concentration (or purity) of the oxygen-enriched gas to be provided to the user.

Another advantage of this method ensures operating conditions of the oxygen separator at highly efficient operating regimes. A highly efficient operating regime is, for example, a regime where the adiabatic compression power input into the separation devices is low. The use of a gas sensor into an equalization duct arranged for monitoring (for instance detecting, for instance measuring) one or more gas components during the "equalization" phase for identifying possible nitrogen breakthrough may be advantageous in operating the PSA system of the at least two oxygen separator devices in the desired highly efficient regimes, controlled by a control device.

A further advantage of this method is that operating an oxygen concentration device close to the separation capacity of the oxygen separation devices ensure for a better energy efficiency of the device.

With respect to further advantages and technical features of the method of generating oxygen it is referred to the description of the oxygen separator, the figures and the description of the figures.

The term oxygen comprising gas, as used herein, may refer to a gas which at least partially comprises gaseous oxygen. Therefore, the term oxygen-enriched gas shall particularly mean a gas which has a higher concentration of gaseous oxygen compared to oxygen comprising gas and could, in its extreme case, consists of pure oxygen gas.

The term oxygen separator, as use herewith, may refer to a part of an oxygen concentrator which is necessary to provide for an oxygen-enriched gas. The oxygen separator comprises, for example, at least two oxygen separation devices, one or more duct, one or more sensors and may be controlled by a control device or a processor.

The term duct, as use herewith, may refer to any canal, tube, pipe, or other means to guide a flow of gas from a point to another.

The term oxygen separation device may refer to a device capable of separating oxygen from an oxygen comprising gas. This may be achieved, for example by filtration, absorption or adsorption. It may, for example, comprises receptacle containing a sorbent material capable of adsorbing nitrogen from the oxygen comprising gas, as well as other impurities, as to provide for an oxygen-enriched gas. The oxygen comprising gas is guided to enter such receptacle by its first end wherein nitrogen and other impurities are adsorbed, wherein the oxygen-enriched gas is outputted.

The term sorbent material means any material capable of adsorbing or absorbing at least one gas. Non limiting example of adsorbing material capable of adsorbing nitrogen from a nitrogen comprising gas (for example ambient air) includes zeolites, such as sodium or lithium zeolites.

The term oxygen concentrator, as used herewith, may refer to a device capable of providing an oxygen-enriched gas to a user. Said device comprises for example an oxygen separator that comprises at least one oxygen separation devices, but also all other means to allow a user to be able to receive an oxygen-enriched gas.

The term flow controller, as used herewith, may refer to a passive valve (that does not require an additional source of energy and may function by mechanical displacement resulting of a sufficient overpressure upstream of the valve) or an active valve (that requires an additional source of energy wherein the valve will be mechanically deflect part of the valve). Such valve(s) may be unidirectional of bi-directional. A flow controller will be understand to be a device which may allow a gas flow, inhibit a gas flow and/or regulate the amount of a gas flow The term first end of the oxygen separation device may refer to the side of the oxygen separator by which the oxygen comprising gas enters said oxygen separator device. Oxygen comprising gas, which may be ambient air, is actively or passively guided toward the first end of the oxygen separation device. Said first end may also be used, in the purging phase of separation, to release a flow of oxygen-deprived gas (nitrogen-enriched gas).

The term second end of the oxygen separation device may refer to the side of the oxygen separator device by which the oxygen-enriched gas exits the oxygen separator device. As an example, the oxygen comprising gas may enter the oxygen separation device by its first end, where component(s) will be adsorb by a sorbent material where an oxygen-enriched comprising gas which will exit the oxygen separator by such second end.

The term sensor as used herewith may refer to any devices capable of monitoring a physical quantity and capable of converting said monitoring data into a signal capable of being read by a control device, a processor or any other means.

The term optimum symmetric operating condition may refer to the operation of the oxygen separation devices near their optimum separation capacity.

The term one parameter of the oxygen separator may refer to any parameters, functions that may have a direct or indirect effect on the oxygen concentration of the oxygen-enriched gas generated by one or more oxygen separation device. For example, but without limitation, said parameter may be the time that the gas takes between the first end and the second end of the oxygen separating devices, the pressure by which the gas go through the different elements of the oxygen separator, the control of the different flow controllers within the oxygen separator, the temperature of the gas inside the oxygen separator, the separation device in use These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF EMBODIMENTS

Certain embodiments will now be described in greater detail with reference to the accompanying drawings. In the following description, like drawing reference numerals are used for like elements, even in different drawings. The matters defined in the description, such as detailed construction and elements, are provided to assist in a comprehensive understanding of the exemplary embodiments. However, the embodiments can be practiced without those specifically defined matters. Also, well known functions or constructions are not described in detail since they would obscure the embodiments with unnecessary detail. Moreover, expressions such as "at least one of", when preceding a list of elements, modify the entire list of elements and do not modify the individual elements of the list. Unless features of "one embodiment" are inconsistent with features of other embodiments, the term "one embodiment" shall be construed to be a disclosure of the associated features in conjunction with all other features that are consistent therewith.

Figure 1:
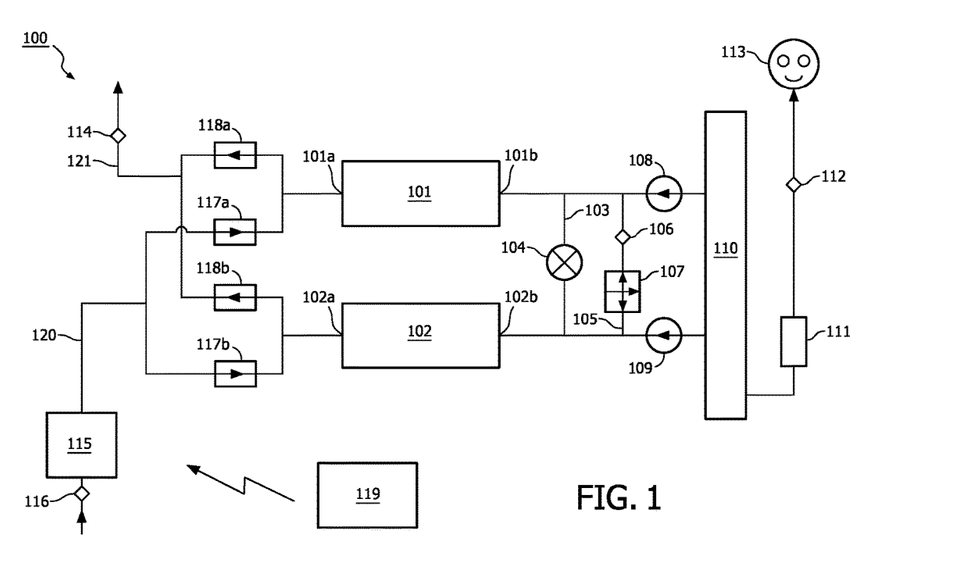
FIG. 1 schematically shows an oxygen separator according to an embodiment of the present invention.

FIG. 1 schematically shows an oxygen separator 100 according to the present invention. Such oxygen separator 100 may be used for generating an oxygen-enriched gas, for example to be administered to a user that is in need of oxygen therapy in view of his physical condition. The oxygen separator 100 is part of an oxygen concentrator (not shown) that may be designed as a stationary arrangement, for example for using it in a hospital, or it may be a portable device, for example for using it in the field of homecare applications. It will be noted that the oxygen separator 100 may furthermore be used for any application at which a high concentration of oxygen, which could be pure or essentially pure, has to be provided, for example in air planes or for welding purposes.

The herein described oxygen separator 100 operation is based on the known process of pressure swing adsorption (PSA). Said process relies on the physical properties of gases which, under high pressure, tend to be adsorbed by solid surfaces. PSA processes is used to separate gases from a gas mixture comprising more than one gases (ambient air being an example) as different gases are attracted to different solid surfaces with a different adsorption coefficients.

An oxygen concentrator (not shown) according to the present invention comprises a compressor or a pump 115 capable of feeding a flow of ambient air (oxygen comprising gas) at high pressure to the oxygen separator 100. More precisely, the filtered flow of ambient air is guided toward the first end of two oxygen separation devices 101, 102 by feeding flow controllers 117a, 117b. Said flow of ambient air is preferably filtered by a filter 116 before being guided by inlet ducts 120 to the oxygen separator 100. Alternatively, the filter may be situated after the compressor 115 generates a high pressure flow of gas.

Each of the at least two oxygen separation devices 101, 102 are filled with an adsorbing material. The respective first end of the two oxygen separation devices 101a, 102a is arranged to receive a filtered flow of ambient air at high pressure during a "feed" phase and is arrange to ventilate flow of nitrogen-enriched gas during a "purge" phase. The "feed" and "purge" phases will be further described below. Such flow of nitrogen-enriched gas is guided by exiting ducts 121 via exiting flow controllers 118a, 118b toward an exit point of the oxygen concentrator (not shown) and is then released in the surrounding area of the user. Alternatively, the nitrogen-enriched gas ventilated during the purge phase may remain in the system and be mixed with the high pressure flow of oxygen comprising gas guided to the first end of the oxygen separation device 101, 102 in the "feed" phase.

In order to proceed with a separation of oxygen from an oxygen comprising gas (for example ambient air) according to the present invention, it is preferable that four distinct phases of the PSA cycle are performed in a cyclic manner, as further described below. Even if those four phases will be described distinctively, the skilled person my foreseen other ways of achieving a similar results and those example shall not be constructed as a limitation of the present invention. For example, the "feed" phase and the "purge" phase may be done simultaneously; in other words, when one of the oxygen separation device 101, 102 is pressurized, into its "feed" phase, the other oxygen separation device 101, 102 is not pressurized, into its "purge" phase. The skilled person will appreciate that to generate an oxygen-enriched gas, it is preferred that the oxygen separation devices 101, 102 work off-phases and in a cyclic manner. This "feed" and "purge" phase are working alternately where in one oxygen separation device 101, 102 is fed with a flow of filtered ambient air at high pressure to be separate and which oxygen separation device 101, 102 is fed with a flow of oxygen-enriched gas at low pressure can be explained by the physical properties of the adsorbing material used in the oxygen separation devices 101, 102, where it is not optimal to have the sorbent material of both oxygen separation devices 101, 102 simultaneously saturated. Alternatively, the two beds could work in phase wherein the ventilation of the nitrogen adsorb by the sorbent material will need to be achieved in an alternative manner as the one described in the present description.

During the "feed" phase, a flow of pressured filtered ambient air is guide via the inlet duct 120 and flow controller 117a, 117b to the first end of one of the oxygen separation device 101a, 102a. As a result of the adsorbing property of the chosen sorbent material contained in the oxygen separation device, the nitrogen comprised in the filtered ambient air will be adsorbed by the adsorbing material and will remain in the oxygen separation device 101, 102. The sorbent material is chosen as such that the oxygen comprised in the filtered ambient air will not be adsorb, or will be limitedly adsorb such that the flow of gas that will exit the oxygen separation device by its the second end 101b, 102b is an oxygen-enriched gas. Said oxygen-enriched gas will then be guided in a purging duct 103 and into a product tank or reservoir 110. The flow of oxygen-enriched comprising gas guided to the purging duct 103 will be used for the "purge" phase while the oxygen-enriched comprising gas is guided to product tank or reservoir 110 by outlet ducts 125 to be delivered to the user 113. The product reservoir 110 to store the oxygen-enriched gas as concentrated by the oxygen separation devices 101, 102 before being administered to a user 113. The flow of oxygen-enriched gas in said product reservoir 110 is regulated by a product flow regulator 108, 109 before it such oxygen-enriched gas is administered to the user 113.

The respective second ends 101a, 102b of the two oxygen separation devices 101, 102 are in fluidic communication via a purge duct 103 which is used in the "purge" phase, said phase will be further explained hereinafter. The "purge" phase has, as a primary objective, to clean the adsorbent material from the previously adsorbed nitrogen. This phase is mainly achieved by a low pressure flow of oxygen-enriched gas guided by the purge duct 103 from the second end 101b, 102b of the oxygen separation device which is in a "feed" phase toward the second end 101b, 102b of the oxygen separation device in a "purge" phase. The "purge" phase is arranged such that a nitrogen-enriched gas flows from the first end 101a, 102a of the oxygen separation device 101, 102 in a "purge" phase toward the exit point of the oxygen concentrator (not shown) via an exit duct 121. The purge duct 103 comprises a purged flow controller 104, preferably a bi-directional flow controller, for allowing the oxygen-enriched gas to flow in the second end of the oxygen separation device 101b, 102b from the oxygen separation device in the "feed" phase to the one in the "purge" phase. It will be understand by the skilled person that this purged flow controller 104 can be active or passive.

In a preferred embodiment according to the present invention, the respective second ends of the two oxygen separation devices 101b, 102b are moreover in fluidic communication via an equalization duct 105. Said equalization duct 105 is preferably only open during an "equalization" phase, which will be further detailed below by the description of FIG. 3. One of the objectives of the "equalization" phase is the equilibrium of the internal pressure of the two oxygen separation devices 101, 102, wherein no pressurized flow of ambient air is guided to any or all of the two first ends of the oxygen separation devices 101a, 102a, alternatively a pressurized flow of ambient air may be guided to any or all of oxygen separation devices 101a, 102a. This equalization duct 105 comprises at lease a sensor 106, preferably a gas sensor, and an equalization flow controller 107. It will be appreciated by the skilled person that the sensor 106 may be situated at any place as to allow monitoring (for instance detecting, for instance measuring) of at least one component of the oxygen-enriched gas that flows into the equalization duct 105. Alternatively, the gas sensor 106 can measure a relative or an absolute concentration of a component of the flow of oxygen-enriched comprising gas that flows into the equalization duct 105. Preferably, the sensor 106 is either an oxygen sensor or a nitrogen sensor. The equalization flow controller 107 is arranged to allow the flow of gas within said equalization duct 105, during the "equalization" phase and blocking the access to the equalization duct 105 during the "feed" and "purge" phases. It will be understood that this arrangement could be foreseen differently by the skilled person, especially if the equalization duct 105 is also, in use, a purging duct. The gas sensor 106 is arranged to detect at least one component of the oxygen-enriched gas during the "equalization" phase, and is in electronic communication with a control device or a processor 119. Said control device 119 is capable of controlling at least one parameter of the oxygen separator.

According to the present example embodiment, in the purging phase, likewise in the feeding phase, the equalization duct does not receive a significant amount oxygen-enriched gas to affect the equalizing sensor 106 measurement. As a result thereof, the control device 119 is not affected by the reading of this equalizing sensor 106 and is then control by other sensor means 114, 112, the purity sensor for example. Alternatively, the equalization sensor 106 could be deactivated, or disabled during the "purge" phase which could rend the use of an equalization flow controller 107 optional, having the equalization duct acting alternatively as a purging duct and an equalization duct.

Figure 2:
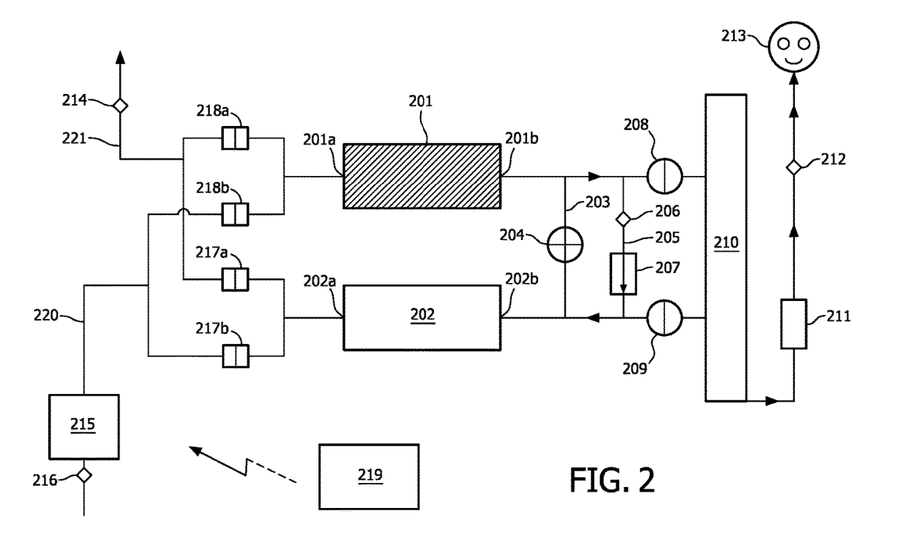
FIG. 2 schematically shows an oxygen separator according to the present invention separator during the "equalization" phase.

FIG. 2 schematically shows an example of an oxygen separator 200 during the "equalization" phase according to the present invention. Such "equalization" phase allows both oxygen separation devices 201, 202 to reach a pressure equilibrium in their relative internal pressure, as both oxygen separation devices 201, 202 are in fluidic communication via a purging duct 203 and a equalization duct 205. In view of their physical properties, the two oxygen separation devices 201, 202 do not have the exact same adsorbing capacities; hence their internal pressure into a similar phase will be different.

In an exemplary scenario, following the "purge" and "feed" phase, one of the oxygen separation devices 201 is over pressurized, while the other oxygen separator device 202 is under pressurized. Moreover, the saturation of the sorbent material contained in each of the oxygen separation devices will be opposed, as the pressurized oxygen separation device 201 is near or have reached its saturation point, while the other oxygen separation device is free or nearly free of nitrogen. The equalization duct 205 is coupled with an equalization flow controller 207, preferably a two-ways flow controller which may be switched between an open and a closed position as a result of the oxygen separation device which was pressurized. This equalization flow controller 207 is arranged to guide a flow of gas from the over pressurized oxygen separation device 201 to the under pressurized oxygen concentration device 202.

Within this "equalization" phase according to the present invention, the compressor (not shown) is not generating a flow of gas in the system, or alternatively, said compressor is generating a low pressure flow of gas, such that the equilibrium between the two oxygen separation devices 201, 202 is not affected. In another embodiment, the compressor is generating a pressurized flow of gas which, via the means of the inlet flow controller 217a, 217b and the inlet duct, is guided to the surrounding areas of the oxygen concentrator (not show), such that no flow is guided through one or more of the oxygen separator devices.

The maximum nitrogen concentration in the "equalization" phases is typically a factor of 2-3 higher than the nitrogen concentration in the "feed" and "purge" phases. Furthermore, the gas volumes exchanged between the separation devices 201, 202 in the "equalization" phases are typically a factor of 2 larger than the gas volumes exiting from the separation devices in the "purge" phase. The first gas sensor 206 is arranged measure at least one component of the flow of gas guided through the equalization duct 205 during the equalization phase. The resulting sensor signal enables a reliable process diagnostics to control the separation process by the control device 219. Such control avoids a "breakthrough" of the nitrogen in the oxygen-enriched comprising gas generated during the "feed" phase, which has the benefit to avoid fluctuations of the oxygen concentration (or purity) of the oxygen-enriched gas and, in an embodiment, to minimize the needed power input. The monitoring by the first gas sensor 206 is arranged to be used by the control device where, as a consequence, one or more parameter of the system may be altered and/or modified.

The monitoring made by the first gas sensor 206 will fluctuate in view of the modification of the operating conditions of the oxygen separator devices 201, 202. The adsorption capability of the sorbent material being influenced by several factors, for example without limitation humidity, temperature, outside pressure, the first sensor 206 arranged to measure at least one component of the flow of gas in the equalization duct 205 allows for a prompt diagnostic of the operating conditions by the control device or processor 219. Several means can be foreseen such that the operating conditions are modified; for example via the compressor 215, the different flow controllers 217a, 217b, the product flow controllers 208, 209, the purged flow controller 204. Alternatively, the time between a change of position of the different flow controllers or the pressure generated by the compressors may be changed.

Even if an oxygen separator 200 may work with only one oxygen separation device, it will be understand by the skilled person that using two oxygen separation devices allows near-continuous production of the oxygen-enriched gas. To allow the equalization phase, the present description discloses at least two oxygen separation devices in fluidic communication with each other such use that oxygen-enriched gas may in the pressurized oxygen separation device to equalize the pressure of the depressurized oxygen separation device as to at least to partially pressurize such second oxygen separation device.

Alternatively to the first gas sensor 206 and the equalization flow controller 207 in the equalization duct, the present invention is not limited to this embodiment and such first gas sensor 206 and such equalization flow controller may be positioned at any place where they are suitable to achieve the function herein described in light of the flow of enriched-oxygen gas in on the equalization duct 205. For example, the first gas sensor 206 may in the vicinity of the equalization duct 205 while the equalization flow controller 207 may be at one of the two extremity openings of the equalization duct.

Preferably, the first gas sensor 206 is either an oxygen sensor or a nitrogen sensor wherein the concentration of either oxygen or nitrogen may be inferred by the control device 219 or any other means capable to do so and providing the data to the control device 219.

Alternatively, in another embodiment of the present invention, such oxygen separator 200 comprises at least two other sensors 214, 212. The exhaust sensor 214 is used to detect and/or measure the composition of oxygen-enriched gas to be administered to the user, while the user sensor 212 is used to detect and/or measure the composition of the gas ventilated from the oxygen separator 201, 202 and to be released into the surrounding environment via at least one exhaust duct (or exit duct) 221.

Within this embodiment, a second gas sensor, such as an oxygen sensor or a nitrogen sensor, for example an optical sensor 214, is provided in the exhaust duct 221 for monitoring the concentration of at least one component of the exhaust gas. It may be preferred that the second gas sensor 214 is positioned in the common exhaust conduct 221, or a respective gas sensor may additionally or alternatively be positioned in the exhaust duct of the first oxygen separation device 201 and/or in the exhaust duct of the second oxygen separation device 202.

Figure 3:
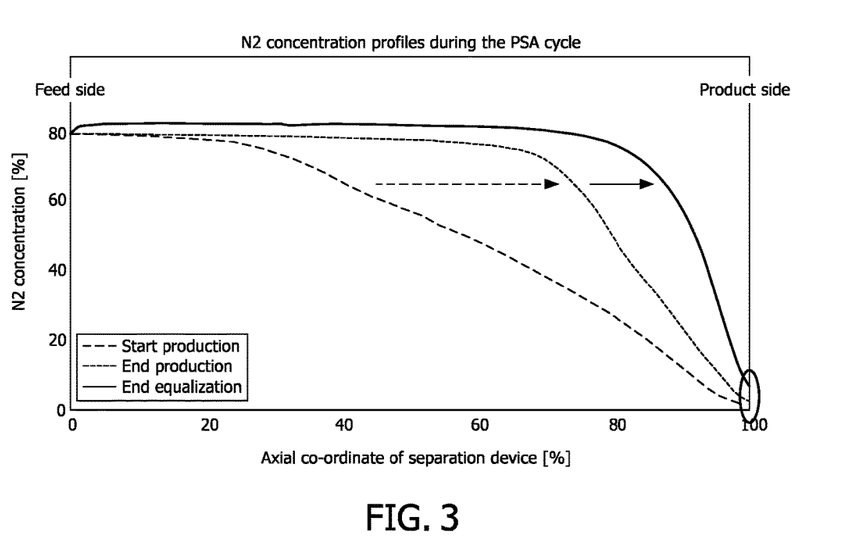
FIG. 3 graphically shows the nitrogen concentration during the "feed" phase relative to the axial co-ordinate of oxygen separation device according to the present invention.

FIG. 3 graphically represents the movement of "mass transfer zone" during production (dotted arrow) and equalization phase (solid arrow). For the purpose of the present application, the "mass transfer zone" shall be understand as the zone of the oxygen separation device where (in this moment of time) nitrogen adsorption is occurring, i.e. the zone where the nitrogen concentration (as plotted in FIG. 3) is increasing from low values (~few %) to the high values (~80%) after adsorption of nitrogen. From FIG. 3 it is clear that the mass transfer zone is progressing during the "feed" phase towards the second end of the oxygen concentration device. So-called "nitrogen breakthrough" (i.e. an increase of the nitrogen concentration in the produced gas) will occur if the mass transfer zone is reaching the second end of the oxygen concentration device. FIG. 3 is also showing that during the "equalization" phase the mass transfer zone is progressing further towards the second end of the oxygen concentration device. Therefore, "nitrogen breakthrough" will first be observed during the "equalization" phase (if a suited sensor is provided within the equalization duct as claimed by the present invention); this means several PSA process cycles before the most unwanted "nitrogen breakthrough" into the gas produced during the "feed" phase would occur.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An oxygen separator for generating a flow of oxygen-enriched gas, the oxygen separator comprising:
at least two oxygen separation devices configured to separate oxygen from an oxygen comprising gas, the at least two oxygen separation devices each comprising a first end for receiving the oxygen comprising gas and a second end for delivering an oxygen-enriched gas;
an equalization duct fluidically coupled to each of the second ends of the at least two oxygen separation devices and configured to equilibrate an internal pressure of the at least two oxygen separation devices;
a first gas sensor provided in the equalization duct, the first gas sensor being configured to monitor a concentration of at least one component of the oxygen-enriched gas in the equalization duct; and
a control device configured to control the oxygen separator based on the monitoring by the first gas sensor.

2. The oxygen separator according to claim 1, wherein the first gas sensor is capable of discrimination between oxygen and nitrogen.

3. The oxygen separator according to claim 1, wherein the control device controls at least one parameter that has an effect on the concentration and/or composition of the oxygen-enriched gas, wherein the at least one parameter comprises one or more of a separation duration, a flow, a pressure, or a selection of one of the at least two separation devices being in use.

4. The oxygen separator according to claim 1, wherein the at least two oxygen separation devices are fluidically coupled to an exhaust duct, and wherein the exhaust duct is fluidically coupled to each of the at least two oxygen separation devices in order to guide an exhaust gas from the at least two oxygen separation devices out of the oxygen separator.

5. The oxygen separator according to claim 4 further comprising a second gas sensor configured to monitor at least one component of the exhaust gas.

6. The oxygen separator according to claim 5 wherein the second gas sensor is configured to monitor the concentration of at least one component of the exhaust gas.

7. The oxygen separator according to claim 5 where the control device is configured to control the oxygen separator based on the monitoring by the first gas sensor and by the second gas sensor.

8. The oxygen separator according to claim 1 further comprising at least one equalization flow controller configured to control an equalization flow of oxygen-enriched gas through the equalization duct.

9. The oxygen separator according to claim 1 further comprising a purging duct fluidically coupling each of the second ends of the at least two oxygen separation devices to one another, the purging duct comprising a purging flow controller configured to control a purging flow of oxygen-enriched gas to the second end of one of the at least two oxygen separation devices.

10. An oxygen concentrator comprising the oxygen separator according to claim 1.

11. A method for separating oxygen from an oxygen comprising gas, the method comprising the steps of:
operating an oxygen separator for generating an oxygen-enriched gas, the oxygen separator comprising at least two oxygen separation devices to separate oxygen from an oxygen comprising gas, wherein the at least two oxygen separation devices each comprise a first end for receiving the oxygen comprising gas and a second end for delivering the oxygen-enriched gas;

equalizing the oxygen separator by generating an equalization flow of oxygen-enriched gas in an equalization duct, the equalization duct fluidically coupling each of the second ends of the at least two separation devices to one another to equilibrate an internal pressure of the at least two oxygen separation devices;

monitoring with a first gas sensor provided in the equalization duct a concentration of at least one component of the oxygen-enriched gas in the equalization duct; and controlling the oxygen separator based on the determination by the first gas sensor via a control device.

12. The method according to claim 11, further comprising the steps of monitoring with a second gas sensor at least one component of the gas in an exhaust duct; and wherein the step of controlling the oxygen separator is further based on the monitoring by the second gas sensor.

13. The method according to claim 11, wherein the step of controlling the oxygen separator comprises controlling at least one parameter of the oxygen separator that has an effect on the concentration and/or composition of the oxygen-enriched gas, wherein the at least one parameter comprises one or more of a separation duration, a flow, a pressure, or a selection of one of the at least two separation devices being in use.

14. An oxygen separator for generating a flow of oxygen-enriched gas, the oxygen separator comprising:

at least two oxygen separation devices configured to separate oxygen from an oxygen comprising gas, the at least two oxygen separation devices each comprising a first end for receiving the oxygen comprising gas during a feed operation and a second end for delivering an oxygen-enriched gas, an equalization duct fluidically coupling each of the second ends of the at least two separation devices to one another, the equalization duct configured to equilibrate an internal pressure of the at least two oxygen separation devices during a equalization operation;

a purging duct fluidically coupling each of the second ends of the at least two oxygen separation devices to one another, the purging duct configured to guide a purging flow of oxygen-enriched gas to the second end of one of the at least two oxygen separation devices during a purge operation;

one or more sensors disposed in the equalization duct, the one or more sensors configured to monitor a concentration of one or more components of the oxygen-enriched gas in the equalization duct; and one or more processors configured by machine-readable instructions to:

interleave the feed operation and the purge operation with the equalization operation;

determine, via the one or more sensors, the concentration of the one or more components of the oxygen-enriched gas during the equalization operation; and adjust one or more operating parameters of the oxygen separator based on the determined concentration, the one or more operating parameters comprising one or more of a separation duration, a flow and/or a pressure of oxygen comprising gas, a flow and/or a pressure of oxygen-enriched gas, or a selection of one of the at least two separation devices being in use.

* * * * *